United States Patent [19]
DePonte

[11] Patent Number: 5,459,452
[45] Date of Patent: Oct. 17, 1995

[54] WET BED AND PATIENT WANDER ALARM SYSTEM WITH SNAP-ON AND MAGNET TRANSMITTER ASSEMBLY

[76] Inventor: Dominic A. DePonte, 9959 Boat Club Rd., N-6, Fort Worth, Tex. 76120

[21] Appl. No.: 18,159

[22] Filed: Feb. 16, 1993

Related U.S. Application Data

[63] Continuation-in-part of Ser. No. 860,324, Mar. 30, 1992, Pat. No. 5,291,181.

[51] Int. Cl.$^6$ ............................................. G08B 21/00
[52] U.S. Cl. ......................... 340/604; 340/573; 128/886; 604/361
[58] Field of Search ................................... 340/604, 605, 340/573; 200/61.04, 61.05; 128/886; 604/361

[56] References Cited

U.S. PATENT DOCUMENTS

| | | | |
|---|---|---|---|
| 3,971,371 | 7/1976 | Bloom | 200/61.04 |
| 4,191,950 | 3/1980 | Levin et al. | 340/604 |
| 5,036,859 | 8/1991 | Brown | 340/573 X |
| 5,137,033 | 8/1992 | Norton | 128/886 |

*Primary Examiner*—Jeffrey A. Hofsass
*Attorney, Agent, or Firm*—Oltman and Flynn

[57] ABSTRACT

A monitoring system for detecting urine includes an electric circuit for activating an indicator, having a break in continuity bordered by a pair of electrodes, a sheet of material for absorbing and retaining urine to permit the urine to provide a conductive path to complete the circuit and activate the indicator, two lead members attached to the sheet of material, the lead members being in a spaced apart relationship from each other, and a mechanism for snap fastening or magnetically fastening each electrode to one lead member. The mechanism for snap fastening includes a male or female snap fastener half attached to one electrode and a female or male snap fastener half attached to the sheet of material and in electrical contact with one lead member, wherein the male snap fastener half can be removably inserted into the female snap fastener half to establish electrical contact between the electrode and the lead member. A monitoring system for detecting the presence of a person in a bed includes an electric circuit for activating an indicator, two spaced apart heat sensors connected to the electric circuit to measure the temperature differential between two different points on the bed, one sensor being positioned at a location on the bed against which a person lying on the bed would recline, and the other the sensor being positioned at a location remote from the heat generated by the person, to indicate by the magnitude of the temperature differential whether a person is occupying the bed.

19 Claims, 4 Drawing Sheets

WET BED AND PATIENT WANDER ALARM SYSTEM WITH SNAP-ON AND MAGNET TRANSMITTER ASSEMBLY

FILING HISTORY

This application is a continuation-in-part of application Ser. No. 07/860,324 filed on Mar. 30, 1992 now U.S. Pat. No. 5,291,181.

BACKGROUND OF THE INVENTION

1. Field of the Invention

The present invention relates generally to the field of systems for detecting liquids on beds, and more specifically to a urine detecting sensor circuit printed on bed pads and bed sheets, diapers and diaper inserts, including a sheet of material having on its upper surface a pair of spaced apart and parallel strips of metallic material, each strip removably connected to a terminal of an alarm circuit with a snap fastener or magnet fastener, the bed pad having a bottom layer of waterproof material, an absorbent middle layer on which the parallel strips would be printed, and a cloth top layer, such that urine deposited on the bed passes through the top layer and soaks the middle layer, providing both the liquid medium and electrolytes necessary to conduct a small electric current between the metallic strips and activate the alarm, and optionally including heat sensors to indicate departure of a patient from his bed, or to indicate wetness or the presence of a high level of moisture by monitoring the temperature differential between two spaced apart sensors.

2. Description of the Prior Art

There have long been wet bed monitoring systems for sounding an alarm when a person urinates on a bed. These systems may sound the alarm when urine is present, but are often so sensitive that they sound false alarms when exposed to even a minute volume of virtually any liquid. They also tend to be difficult and expensive to manufacture and highly labor intensive to routinely clean.

Examples of such a prior art system include those of Wilson, U.S. Pat. No. 4,356,479, issued on Oct. 26, 1982, and Wilson U.S. Pat. No. 4,271,406, issued on Jun. 2, 1981. Both Wilson devices feature electrodes fabricated from permanent magnets which are held apart by a thin spacer. These magnets are attached to a patient's clothing or bed sheet. Urine completes the circuit between the electrodes to sound an alarm. A problem with Wilson is that the extent of the monitored area when a magnet is attached to a bed sheet is limited to the dimensions of the magnet, and if a patient happens to roll away from that spot and urinates elsewhere, the condition goes undetected. There is also some risk of danger from electric shock where the preferred embodiment including alternating current and the fuse system is employed. Finally, patient mobility is restricted where the option of attachment to the patient's garment is used, because the apparatus must be removed each time the patient gets out of bed.

Regal, U.S. Pat. No. 4,163,449, issued on Aug. 7, 1979, teaches a device which provides an aversive stimulus to a child who bed wets while asleep. Regal includes a urine detection pad of absorbent material having wire screen electrodes on either side of the pad which trigger an alarm when even a small amount of urine is present. A problem with Regal is that the sensor pad would react to any liquid, such as pure water, if soaking causes the wire screens to engage each other. Another problem with Regal is that it is designed to condition a child with an unpleasant sound rather than to alert a nurse or other health care worker at a distance.

Bloom, U.S. Pat. No. 3,971,371, issued on Jul. 27, 1976, discloses a urine sensing pad including a sheet of flexible insulating material carrying an array of conductive sensor strips on both of its faces. Moisture makes the electrical connection between the sensor strips to activate an alarm. A problem with Bloom is that the sensor strips are formed of aluminum tape and fastened to a Mylar pad with staples, which is a fragile construction. Cleaning such an arrangement is difficult, because urine seeps between the pick-up strips and sensor strips. Bacteria can be secluded among the layers, causing potential health problems. Another problem with Bloom is its complicated construction.

Campbell, U.S. Pat. No. 2,907,841, issued on Oct. 6, 1959, discloses a flexible support of dielectric material having crosswise electrodes traversing the width of the support. Alternate crosswise electrodes are attached to the different terminals of the circuit and the circuit is completed when an electrolyte shorts these electrodes, activating an alarm. A problem with Campbell is that free flowing urine is used to activate the device, so that the user must lye in this unabsorbed wetness until help arrives. Campbell is also cumbersome to build, uncomfortable to sleep on because nothing cushions contact with the electrodes and support, and it is difficult to clean. The metal foil is vulnerable to damage from rough handling.

McKenzie, U.S. Pat. No. 2,866,454, issued on Dec. 30, 1958, teaches metal grids of bronze wire; a plastic sheet and a pad to deliver shock treatment to a patient. A problem with McKenzie, apart from its design to shock rather than merely signal, is that it is clumsy and of intricate construction. Low reliability and high manufacturing costs are likely.

Seiger, U.S. Pat. No. 2,644,050, issued on Jun. 30, 1953, discloses a flat, thin, waterproof electro-insulative pad having embedded in its top face several thin metal conductors forming separated electrodes. The presence of urine shorts the electrodes and activates a signal. A problem with Seiger is that moisture is retained against the patient's skin while the signal is triggered. Another problem is that the caustic urine would quickly corrode the rubber and tin materials. Still another problem is that urine would seep into all the many crevices and make cleaning difficult and time consuming.

Kroening, U.S. Pat. No. 2,726,294, issued on Dec. 6, 1955, teaches two elongated flat thin plates of cardboard material, having metallic coatings on either side of the material. A problem with Kroening is that it would be difficult to clean urine from this multi-layer construction. Single use followed by disposal, on the other hand, would make Kroening prohibitively expensive to use. Another problem is that it is cumbersome to build and uncomfortable to sleep on.

Norton, U.S. Pat. No. 5,137,033, issued on Aug. 11, 1992 teaches a patient monitoring device which signals a health care worker with an alarm if moisture is detected. A problem with Norton is that it has numerous wires and is cumbersome. Another problem with Norton is that a nurse's aid has to manually wash and disinfect the pad, which is costly in work time and unpleasant. Additionally, a cloth insert has to be laundered after each use.

It is thus an object of the present invention to provide a moisture monitoring system which is activated only by urine and a limited number of other liquids.

It is another object of the present invention to provide such a monitoring system which is comfortable and which draws urine away from the user to minimize irritating contact with the skin.

It is a further object of the present invention to provide a temperature monitoring system with a single heat sensor which is activated by a fever level temperature of a patient or by a temperature level which indicates patient discomfort.

It is a further object of the present invention to provide a temperature monitoring system, optionally incorporating two heat sensors, which measures the temperature differential between the two heat sensors to detect wetness or a high degree of moisture.

It is still another object of the present invention to provide such a monitoring system which is durable and easily cleaned for reuse.

It is finally an object of the present invention to provide such a monitoring system which is comparatively simple in design and inexpensive to manufacture.

SUMMARY OF THE INVENTION

The present invention accomplishes the above-stated objectives, as well as others, as may be determined by a fair reading and interpretation of the entire specification.

A monitoring system is provided for detecting urine, including an electric circuit for activating an indicator, having a break in continuity bordered by a pair of electrodes, a sheet of material for absorbing and retaining urine to permit the urine to provide a conductive path to complete the circuit and activate the indicator, two lead members attached to the sheet of material, the lead members being in a spaced apart relationship from each other, and a mechanism for snap fastening each electrode to one lead member. The mechanism for snap fastening each electrode includes a male or female snap fastener half attached to one electrode and a female or male snap fastener half attached to the sheet of material and in electrical contact with one lead member, wherein the male snap fastener half can be removably inserted into the female snap fastener half to establish electrical contact between the electrode and the lead member. Alternatively, the mechanism for snap fastening each electrode includes a male or female snap fastener half attached to one electrode, a hole in the lead member for receiving a male snap fastener half, and a female or male snap fastener half for snapping over the male snap fastener half so that the lead member is secured between the male and female snap fastener halves. The sheet of material is preferably a hydrophilic material. The sheet of material may be a bed sheet. The sheet of material may be contained between two other sheets of material which together constitute a bed pad. The sheet of material may be a nylon cloth strip or an elastagen or a disposable diaper insert pad. The indicator preferably includes an indicator light. Alternatively, the indicator includes a sound generator. The system may additionally include a flexible sheet of waterproof material to which the lead members are joined. The flexible sheet of waterproof material optionally fits into a pocket of a bed pad. The system may additionally include a heat sensor for monitoring the temperature of a person resting against the sheet of hydrophilic material. The system also preferably includes a water-permeable cover sheet which extends across a side of the sheet of hydrophilic material opposite the lead members. Several of these systems may be independently monitored at a single annunciator panel or nurses station, or a single remote transmitter and receiver unit.

A monitoring system is also provided for detecting the presence of a person in a bed, including an electric circuit for activating an indicator, two independent and spaced apart heat sensors connected to the electric circuit to measure the temperature differential between two different points on the bed, one sensor being positioned at a location on the bed against which a person lying on the bed would recline, and the other sensor being positioned at a location remote from the heat generated by the person, which would reflect room temperature or ambient temperature, to indicate by the magnitude of the temperature differential whether a person is occupying the bed.

A monitoring system is also provided for detecting urine, which includes a transmitter including an electric circuit for activating an indicator, having a break in continuity bordered by a pair of electrodes, a sheet of material for absorbing and retaining urine to permit the urine to provide a conductive path to complete the circuit and activate the indicator means, two lead members attached to the sheet of material, the lead members being in a spaced apart relationship from each other, and a mechanism for securing the sheet of material to the transmitter. The mechanism for securing may include a magnetic member attached to the transmitter and a magnet attracting metal member attached to the sheet of material. Alternatively the mechanism for securing includes a spring-biased clip attached to the transmitter and having teeth for making electrical contact with the lead members. Grommets may be provided on the lead members and the teeth of the spring-biased clip may be rounded for entry into the grommets.

BRIEF DESCRIPTION OF THE DRAWINGS

Various other objects, advantages, and features of the invention will become apparent to those skilled in the art from the following discussion taken in conjunction with the following drawings, in which.

DETAILED DESCRIPTION OF THE PREFERRED EMBODIMENTS

Figures 1, 2:
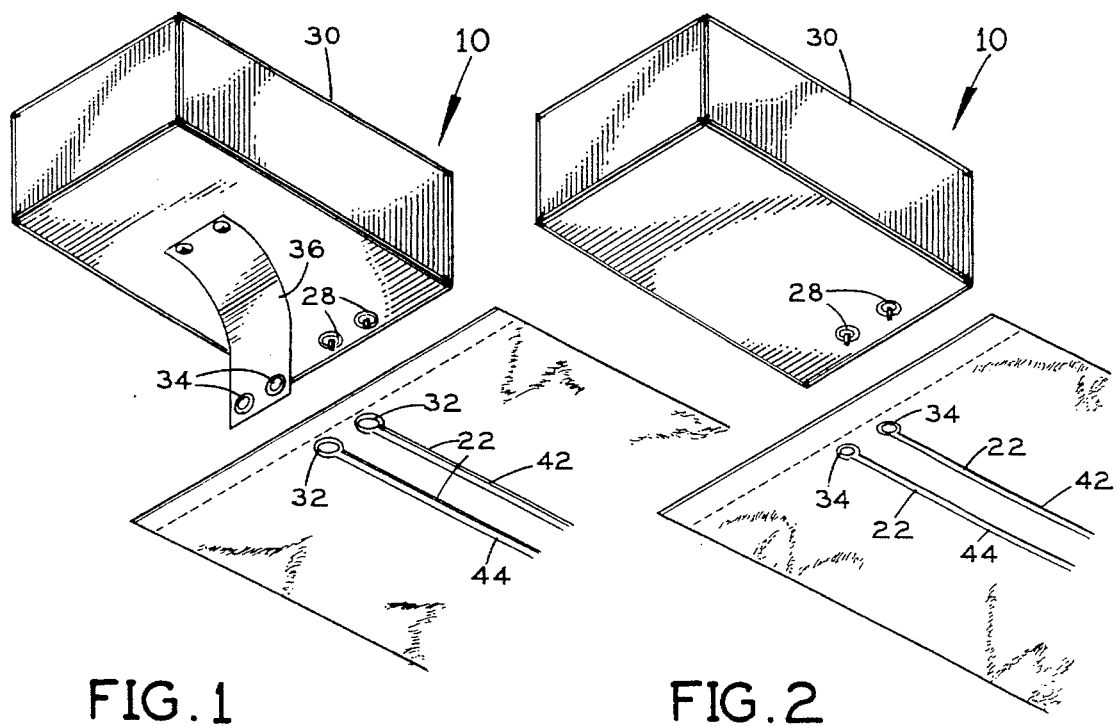
FIG. 1 is a perspective view of the inventive transmitter assembly equipped with male fastener-half electrodes and female fastener halves mounted on a ribbon, and conductive strips having fastener receiving holes.
FIG. 2 is a perspective view of the inventive transmitter assembly equipped with male fastener-half electrodes and female fastener halves mounted on the conductive strips themselves.
Figures 3, 4:
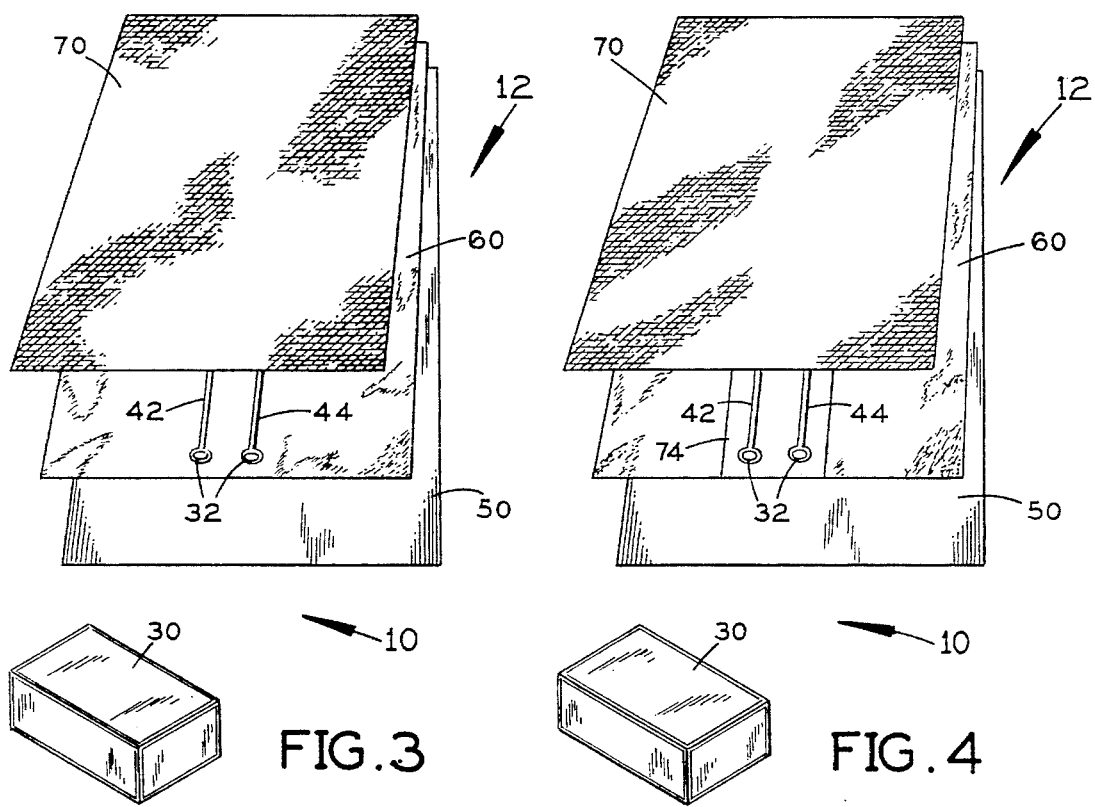
FIG. 3 is a perspective, cut-away view of the inventive disposable bed pad, showing the three layers, and the conductive strips on the middle layer.
FIG. 4 is a perspective, cut-away view of the inventive non-disposable bed pad, showing the three layers, and the inventive sensor pad attached to the middle layer.
Figures 5, 6:
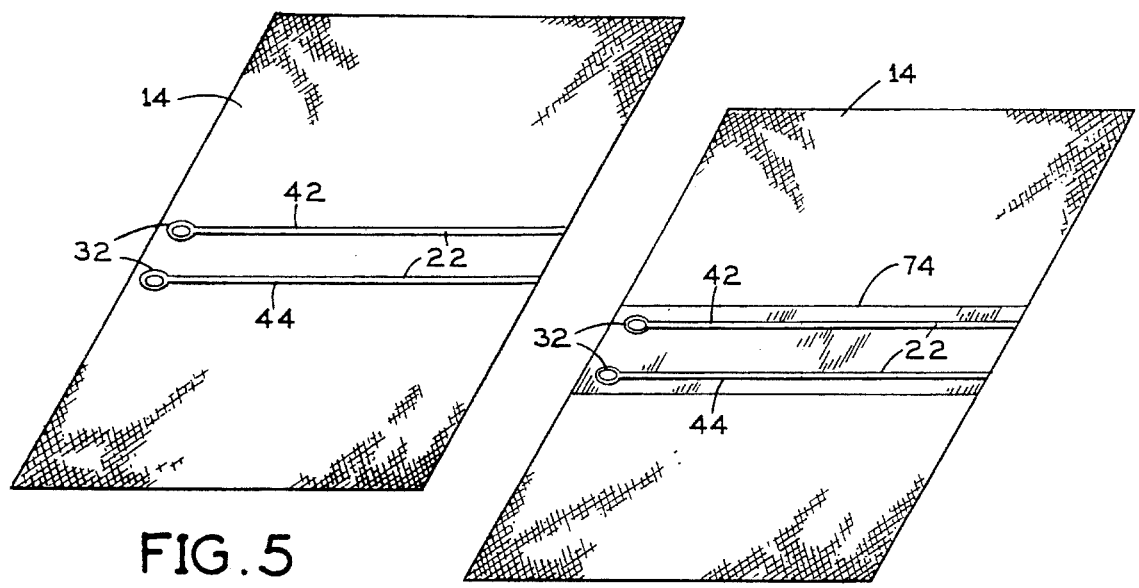
FIG. 5 is a perspective view of the inventive disposable bed sheet with the conductive strips bonded to its bottom surface.
FIG. 6 is a perspective view of the inventive non-disposable bed sheet with the launderable or removable sensor pad bonded to its bottom surface.
Figures 7, 8, 8A:
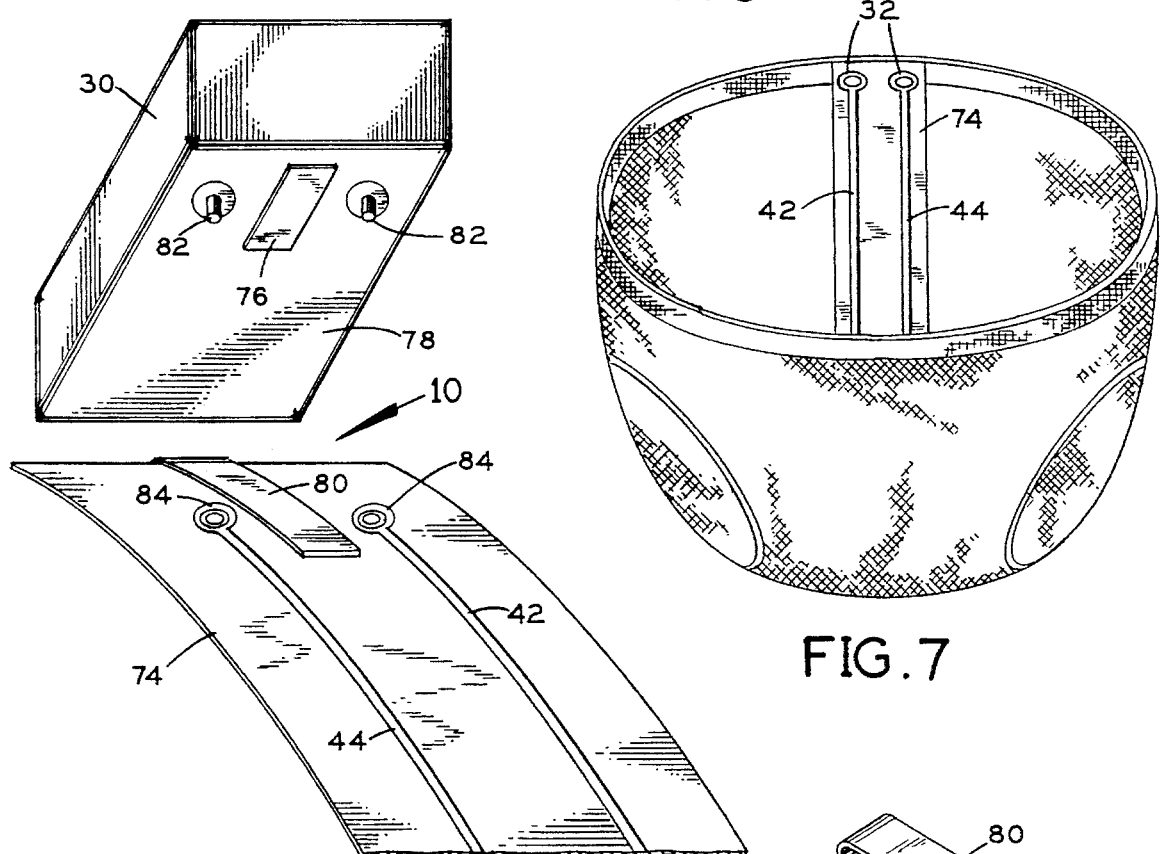
FIG. 7 is a perspective view of a diaper for a child or adult equipped with the inventive sensor pad.
FIG. 8 is a perspective view of another embodiment of the inventive transmitter assembly and sensor pad, having the magnetic strip, electrode stem and grommet features, suitable for all bed pads and sheets.
FIG. 8a is a perspective view of the conductive clip for attachment to a bed pad or sheet.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

PREFERRED EMBODIMENTS

Referring to FIGS. 1–8, a moisture monitoring system 10 is disclosed for use in hospitals, nursing homes and private homes. System 10 includes a bed pad 12 or bed sheet 14 comprising an alarm circuit 22 and a transmitter assembly 30 which snaps on to bed pad 12 or sheet 14. Bed pad 12 and sheet 14 may be either disposable or non-disposable, as described more fully below. Alarm circuit 22 is completed and activated by the presence of a quantity of liquid containing an electrolyte which conducts current between the electrodes. Urine can activate the alarm because it contains an electrolyte.

While a single alarm may be activated at the bed 26 itself, or on the doorway of the room where bed 26 is located, it is preferred that several beds 26 be so equipped and their circuits 22 all linked to a central monitoring board. Such a board might be located at a nurses' station.

Alarm circuit 22 preferably includes a sheet of material onto which two parallel conductive strips 42 and 44 of metallic material are laminated, vulcanized, painted, silk-screen printed or glued. Strip 42 is connected to a positive electrode and strip 44 is connected a negative electrode of circuit 22. Circuit 22 is powered by a 12 volt battery contained within a remote transmitter assembly 30. The distance between strips 42 and 44 depends on the current required to operate compatibly with the transmitter. Transmitter assembly 30 includes two male snap fastener halves 28 which connect to strips 42 and 44. This is preferably accomplished in one of two ways. In one instance, a hole 32 is provided in each strip 42 and 44, and male fastener halves fit through holes 32. Then two female snap fastener halves 34 connected to transmitter assembly 30 with a ribbon 36 snap over male fastener halves 28, thereby securing them through holes 32. See FIG. 1. Alternatively, female fastener halves 34 are structurally and electrically joined to strips 42 and 44, and male fastener halves 28 snap directly into them. See FIG. 2. Transmitter assembly 30 sends a wireless signal to a board, which is a receiver annunciator panel, or to a single receiver unit. The indicator activated may be a siren or bell alarm, or a colored light. Other embodiments of transmitter assembly 30 are described below under a separate heading.

I. Disposable Bed Pad

One embodiment of inventive system 10 takes the form of a disposable bed pad 12 which preferably includes three layers of material. See FIG. 3. These layers include a waterproof, plastic bottom layer 50, an absorbent middle layer 60 of wet strength tissue paper, and a hydrophilic top layer 70. Strips 42 and 44 are printed onto middle layer 60 as metallic ink consisting of a 70–30 or 60–40 mix of silver and carbon ink or paint. This metallic ink or paint is a colloidal substance. When disposable bed pad 12 becomes soiled, it is removed from transmitter assembly 30 simply by unsnapping fasteners 28 and 34. Transmitter assembly 30 operates on high frequencies so that the sensitivity of the system can be adjusted to delay the alarm signal, even until pad 12 is fully wet if desired.

Bed pad 12 may be the size of a conventional bed pad, or may equivalently be much smaller, for positioning under the posterior of a bed occupant. The smaller version of bed pad 12 requires a conductive member to connect bed pad 12 to transmitter assembly 30. The preferred conductive member for this purpose is what is known as a ribbon cable. Transmitter assembly 30 may connect to a first end of the ribbon cable by fitting between opposing faces of two ribbon members protruding from assembly 30. The ribbon members may have fasteners which snap over or into the ribbon cable to both structurally connect to and make electrical contact with the ribbon cable. The second end of the ribbon cable may in turn split into a pair of ribbon members like those on assembly 30, complete with fasteners, to connect structurally and electrically to the circuit elements of bed pad 12. The fasteners on the ribbon cable may for example snap through holes in the strips 42 and 44 of the circuit on bed pad 12. A ribbon cable is wide and flat, and thus does not create an uncomfortable bulge under a bed occupant. The smaller version of bed pad 12 may also be described as a sensor pad.

II. Non-Disposable Bed Pad

Non-disposable bed pad 12 is like disposable bed pad 12, except for the following differences. A sensor pad 74 is provided in the form of a narrow strip of nylon fabric or elastomer material extending the full width of bed pad 12. Strips 42 and 44 are attached to sensor pad 74. Sensor pad 74 is sewn to middle layer 60. Then middle layer 60 is placed over bottom layer 50, and top layer 70 is placed over middle layer 60, and the layers are sewn together. See FIG. 4.

Strips 42 and 44 must be sufficiently durable to withstand the rigors of ordinary laundering. Several ways of achieving this durability are contemplated. An elastomeric material that may be printed with carbon and silver ink. Alternatively, a silver based coating may be vulcanized over a silicone core. Another suitable strip material is conductive, woven scrim-nylon mesh, impregnated with silver and palladium, a by-product of platinum. Still another suitable strip material is highly conductive Flex-o-Shield™ elastomer consisting of a silicon rubber binder filled with irregularly shaped silver plated copper particles. Finally, the strips may be formed of silver-plated glass particle silicone.

III. The Bed Pads Generally

Layer 60 absorbs and retains urine, so that the urine is both drawn away from the patient and can serve to conduct current to activate circuit 22. This is a key inventive feature of system 10 because a small quantity of moisture, such as from perspiration, would not soak layer 60 sufficiently to make an electrical connection between strips 42 and 44. Where layer 60 is one quarter inch thick, prototype testing has revealed that one half cup to one cup of urine is needed to activate the alarm, but this varies depending on the type of hydrophilic material used and layer 60 thickness. Since the volume of urine discharged by a human being is almost invariably in excess of one cup, reliability is maintained while false alarms are minimized or eliminated. No less important is that ordinary spilled water does not activate the circuit and cause a false alarm. Urine is necessary because it provides the electrolytes needed as charge carriers. In contrast, a thimble-full of virtually any liquid would activate many of the prior art wet bed alarm devices.

Top layer 70 passes but does not substantially absorb liquids. Layer 70 helps separate the skin of the patient from the soaked middle layer 60 to minimize exposure to moisture and resulting irritation. Layer 70 also provides a durable outer surface for bed pad 12 for an increased useful life.

In summary, when a person wets bed 26, the urine passes through top layer 70 and soaks middle layer 60. Bottom layer 50 prevents the urine from reaching the mattress. The urine conducts electric current from strip 44 to strip 42 and thereby completes alarm circuit 22. The battery pack is energized as a result and circuit 22 then activates wireless transmitter assembly 30. Transmitter assembly 30 emits an electromagnetic signal of radio wavelength to a receiver which activates an indicator at the board. The board is preferably located and monitored at a nurses' station. This permits prompt action to be taken to remove and replace the patient's wet clothing and bed pad 12.

IV. Disposable Bed Sheet

Silver-carbon ink is preferably printed directly onto the bottom surface of a disposable bed sheet 14 to form strips 42 and 44. See FIG. 5. Alternatively, strips 42 and 44 are on a sheet sensor pad 74, similar to that described above for non-disposable bed pads 12 except that nylon is not used. Sensor pad 74 is bonded to the bottom surface of bed sheet 14. Bed sheet 14 should be a fitted sheet, so that strips 42 and 44 stay properly positioned. This disposable embodiment is well suited for AIDS control.

V. Non-Disposable Bed Sheet

For a non-disposable bed sheet 14, sensor pad 74 is attached to the bottom surface of bed sheet 14, either by sewing or with a heat bond, and extends across the width of bed sheet 14. See FIG. 6. In this instance strips 42 and 44 must be formed of launderable materials, such as those described above for the non-disposable bed pad 12. Alternatively, sensor pad 74 may be removably attached to bed sheet 14 with an adhesive, so that pad 74 can be discarded when soiled. Fitted bed sheets 14 are once again preferred, for the above-stated reasons.

In all of these various applications, circuit 22 may also be incorporated with a smaller version or size of bed pad 12 into a wheel chair, a child's crib, a belt, a disposable or non-disposable diaper or other garment. Alternatively, sensor pad 74 may be stitched or adhesively attached to these items, with transmitter assembly 30 located within a pocket in the item. See FIG. 7.

VI. Other Transmitter Preferred Embodiments

Transmitter assembly 30 may have a magnetic strip 76 attached to its top side 78 between the electrodes, preferably with a suitable glue. See FIG. 8. A corresponding clip member 80 is provided on sensor pad 74 or directly on bed pad 12 or bed sheet 14, between conductive strips 42 and 44, for removable engagement by magnetic strip 76. Clip member 80 may be a strip of metal glued to pad 12 or sheet 14, or a resilient, folded clip which fits around and resiliently grasps pad 12 or sheet 14. Member 80 may also be pinched together or otherwise attached with hook and loop fasteners such as VELCRO™. See FIG. 8a.

For securing assembly 30 to all embodiments of bed pad 12 and bed sheet 14, stems 82 may protrude from the electrodes for insertion into conductive grommets 84 in strips 42 and 44. See FIG. 8. Fitting electrode stems 82 into grommets 84 creates electrical contact between strips 42 and 44 and the electrodes. The attraction between magnetic strip 76 and clip member 80 removably holds transmitter assembly 30 against pad 12 or sheet 14.

Figure 9:
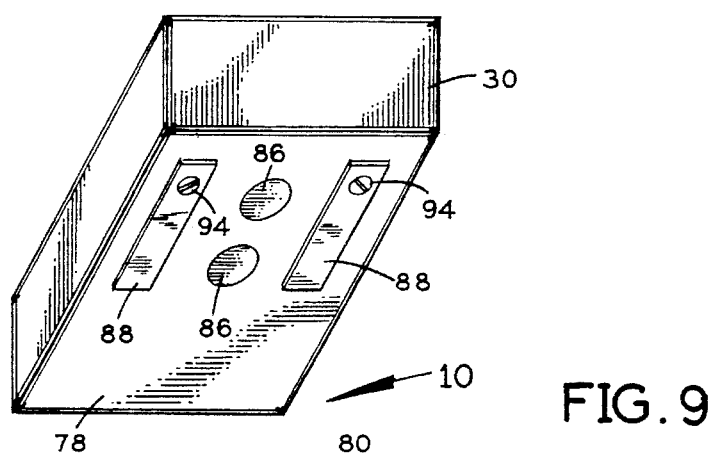
FIG. 9 is a perspective view of an embodiment of the transmitter assembly similar to that of FIG. 8. The magnetic strip is replaced with separate magnets and the electrode stems are replaced with conductive elastomeric strips, suitable for disposable bed sheets.

For securing assembly 30 to a disposable bed sheet 14 specifically, magnet strip 76 is preferably replaced with two discrete magnets 86. Magnets 86 are recessed so that they are flush with the top side 78 of transmitter assembly 30. See FIG. 9. Stems 82 are replaced with conductive bands 88 on either side of magnets 86 for making broad contact with conductive strips 42 and 44. Bands 88 are preferably formed of a conductive elastomer such as FLEX-O-SHIELD™ and each attached with glue to top side 78 and to the electrodes with one brass screw 94. This arrangement is well suited for use with disposable sheets 14, because the expense of structural features such as grommets 84 is avoided.

Figure 10:
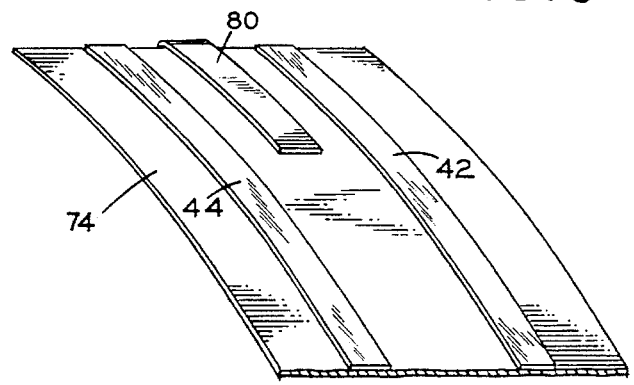
FIG. 10 is a perspective view of the spring clip variation of the transmitter assembly, having rounded teeth for insertion into grommets provided in the conductive strips.
Figure 10:
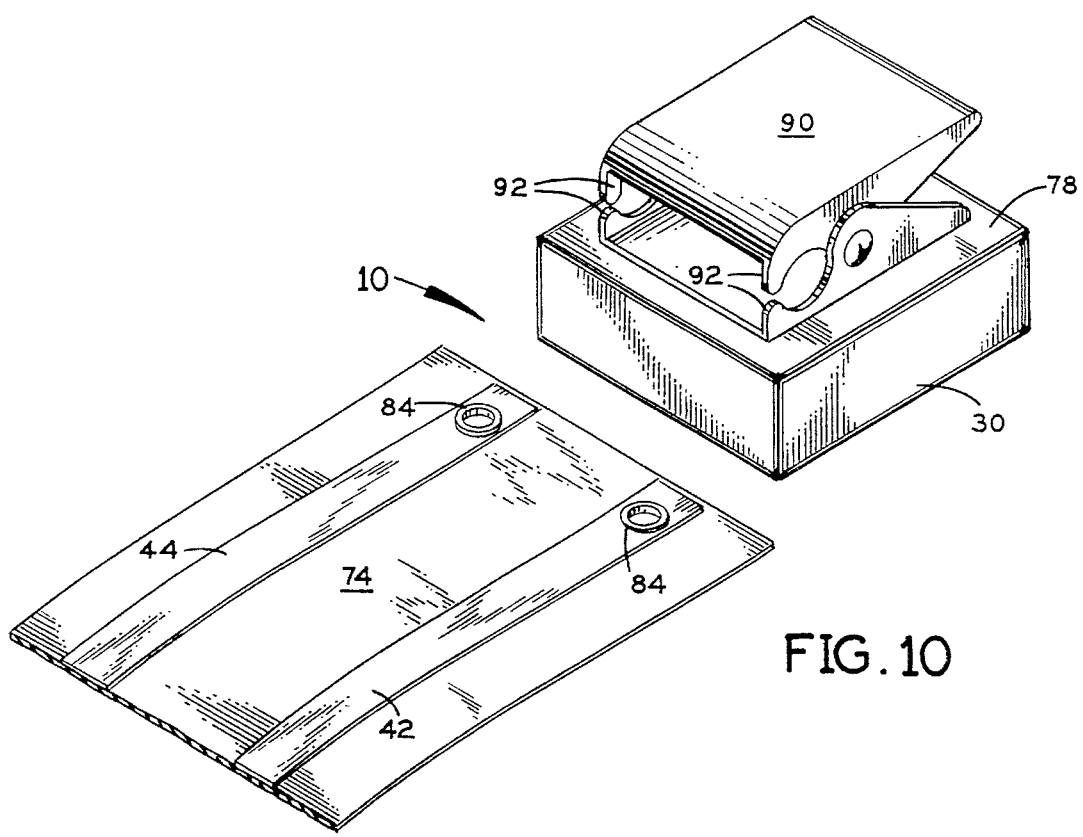
Figure 11:
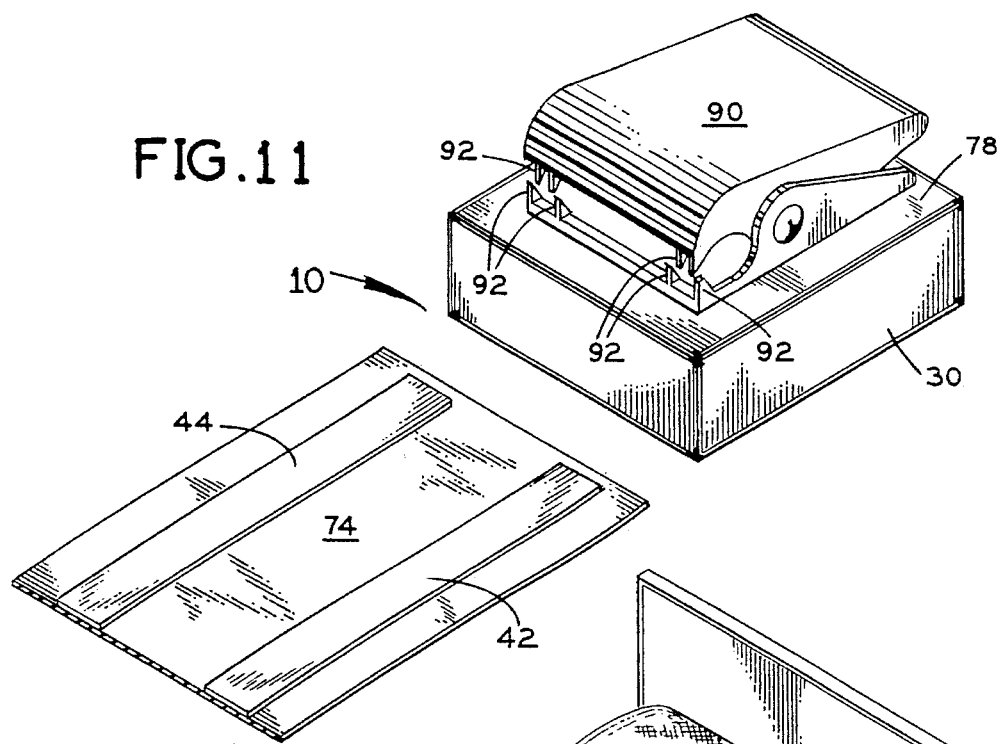
FIG. 11 is a perspective view of the spring clip variation as in FIG. 10, except that jagged teeth are provided for use on bed pads and sheets not having grommets.

Finally, transmitter assembly 30 may have a spring clip 90 attached to its top side 78. Teeth 92 on spring clip 90 are electrically connected to the assembly 30 electrodes. Where pads 12 or sheets 14 have grommets 84 in strips 42 and 44, rounded teeth 92 are provided to fit inside grommets 84, as did stems 82. See FIG. 10. Where pads 12 or sheets 14 have no grommets 84, sharp teeth 92 similar to staples are provided to penetrate and make contact through bed pad 12 material with strips 42 and 44, provided on middle layer 60. See FIG. 11.

VII. Patient Wander Alarm

Figure 12:
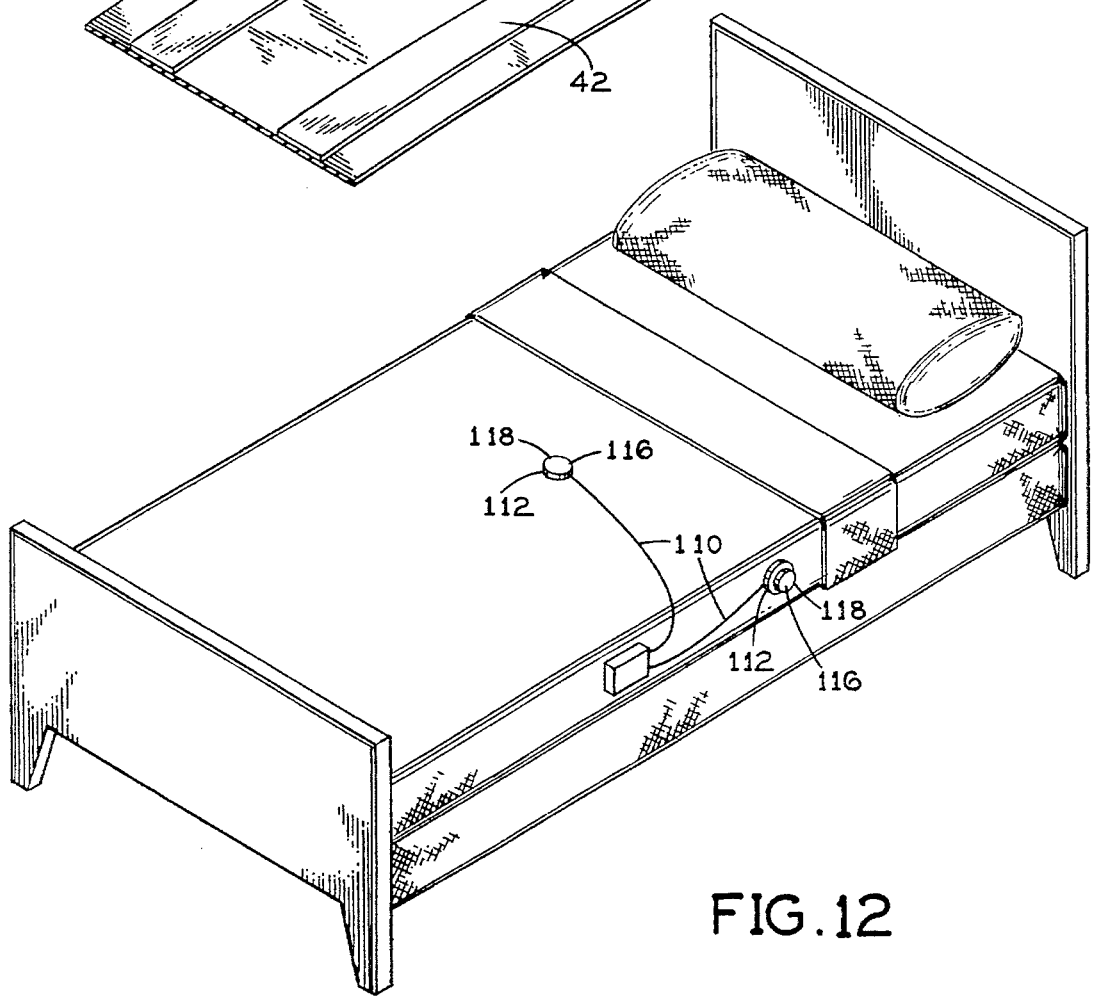
FIG. 12 is a perspective view of a bed equipped with the patient wander alarm system, showing a heat sensor on the top of the bed and another heat sensor on the side of the bed.

A system 100 is provided to detect the departure of a patient from his bed. See FIG. 12. System 100 includes a circuit 110 having two separate and independent heat sensors 112, preferably thermistors because of their minimal size and cost. Alternatively, each heat sensor 112 may be an SS washer thermocouple with teflon insulated leads and 20 gage elements produced by Nanmac, each mounted under a button 116. The top surface 118 of each button 116 is preferably covered with the hook or loop portion of a hook and loop fastener material such as VELCRO™.

Sensors 112 work in concert to achieve their purpose. The difference in temperature between sensors 112 is continuously measured. One sensor 112 is on bed 26 and positioned to make thermal contact with a patient reclining in bed 26, and a second sensor 112 is positioned on the side of or under the bed, out of thermal contact with the patient. The heat from the patient creates a temperature differential between the two sensors 112. When the patient leaves the bed, the differential diminishes to a preprogrammed value, activating an indicator which alerts a nurse.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

PARTS LIST

10. Monitoring system
12. Bed pad
14. Bed sheet
22. Alarm circuit
26. Bed
28. Male fastener half
30. Transmitter assembly
32. Holes in strips 42 and 44
34. Female fastener half
42. Strip connected to positive electrode
44. Strip connected to negative electrode
50. Bottom waterproof layer of bed pad 12
60. Middle absorbent layer of bed pad 12
70. Top layer of bed pad 12
74. Sensor pad
76. Magnetic strip
78. Transmitter assembly top side
80. Clip member
82. Stems on electrodes
84. Grommets
86. Magnets (two, separate)
88. Conductive elastomeric bands on top side 78
90. Spring clip with teeth
92. Teeth in spring clip 90
94. Brass screws
100. System
110. Heat sensing circuit
112. Heat sensors
116. Button for 112
118. Top surface of 116

I claim as my invention:

1. A monitoring system for detecting urine, comprising:
an electric circuit for activating indicator means, having a break in continuity bordered by a pair of electrodes,
a sheet of material for absorbing and retaining urine to permit said urine to provide a conductive path to complete said circuit and activate said indicator means, wherein said sheet of material is contained between two other sheets of material which together constitute a bed pad,
two lead members attached to one of said sheets of material, said lead members being in a spaced apart relationship from each other,
means for snap fastening each said electrode to one of said two lead members.

2. A monitoring system according to claim 1, wherein said means for snap fastening each said electrode comprises:
a male snap fastener half attached to one said electrode,
a female snap fastener half attached to said sheet of material and in electrical contact with one said lead member, wherein said male snap fastener half can be removably inserted into said female snap fastener half to establish electrical contact between said electrode and said lead member.

3. A monitoring system according to claim 1, wherein said means for snap fastening each said electrode comprises:
a male snap fastener half attached to one said electrode,
a hole in said lead member for receiving said male snap fastener half,
a female snap fastener half for snapping over said male snap fastener half so that said lead member is secured between said male and female snap fastener halves.

4. A monitoring system according to claim 1, wherein said means for snap fastening each said electrode comprises:
a female snap fastener half attached to one said electrode,
a male snap fastener half attached to said sheet of material and in electrical contact with one said lead member, wherein said male snap fastener half can be removably inserted into said female snap fastener half to establish electrical contact between said electrode and said lead member.

5. A monitoring system according to claim 1, wherein said means for snap fastening each said electrode comprises:
a female snap fastener half attached to one said electrode,
a hole in said lead member for receiving a male snap fastener half,
a male snap fastener half for snapping over said male snap fastener half so that said lead member is secured between said male and female snap fastener halves.

6. A monitoring system according to claim 1, wherein the sheet of material is hydrophilic material.

7. A monitoring system according to claim 1, wherein said one of said sheets of material is a nylon cloth strip.

8. A monitoring system according to claim 7, additionally comprising an inner sheet of material, wherein said nylon cloth strip is attached with attachment means to said one of said sheets of material.

9. A monitoring system according to claim 8, wherein said attachment means is fibrous stitches.

10. A monitoring system according to claim 8, wherein said attachment means is an adhesive material.

11. A monitoring system according to claim 7, wherein said nylon cloth strip is attached with attachment means to one other said sheet, wherein said attachment means is fibrous stitches.

12. A monitoring system according to claim 7, wherein said nylon cloth strip is attached with attachment means to one other said sheet, wherein said attachment means is an adhesive material.

13. A monitoring system according to claim 1, wherein said indicator means comprise an indicator light.

14. A monitoring system according to claim 1, wherein said indicator means comprise sound generating means.

15. A monitoring system according to claim 1, additionally comprising a water-permeable cover sheet which extends across a side of said sheet of hydrophilic material opposite said lead members.

16. A monitoring system according to claim 1, wherein several said systems are independently monitored at a single annunciator panel.

17. A monitoring system according to claim 1, wherein said sheet of material is an elastomer.

18. A monitoring system according to claim 17, additionally comprising a bed sheet having a bottom surface, wherein said nylon cloth strip is attached with attachment means to said bottom surface of said bed sheet.

19. A monitoring system according to claim 17, additionally comprising a bed pad having an inner sheet of material, wherein said nylon cloth strip is attached with attachment means to said inner sheet of material.

* * * * *